United States Patent
Hsieh

(10) Patent No.: US 9,993,219 B2
(45) Date of Patent: Jun. 12, 2018

(54) X-RAY ANTI-SCATTER GRID WITH VARYING GRID RATIO

(71) Applicant: Scott Hsieh, Anaheim, CA (US)

(72) Inventor: Scott Hsieh, Anaheim, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 201 days.

(21) Appl. No.: 15/073,909

(22) Filed: Mar. 18, 2016

(65) Prior Publication Data

US 2016/0328836 A1 Nov. 10, 2016

Related U.S. Application Data

(60) Provisional application No. 62/134,991, filed on Mar. 18, 2015.

(51) Int. Cl.
*A61B 6/00* (2006.01)
*G21K 1/02* (2006.01)
*G06T 11/00* (2006.01)

(52) U.S. Cl.
CPC .......... *A61B 6/5282* (2013.01); *A61B 6/4291* (2013.01); *G06T 11/008* (2013.01); *G21K 1/025* (2013.01); *G06T 2207/10081* (2013.01); *G06T 2207/30168* (2013.01)

(58) Field of Classification Search
CPC ... A61B 6/5282; A61B 6/4291; A61B 6/4233; A61B 6/4035; G21K 1/025; G21K 2207/005; G06T 11/008
See application file for complete search history.

(56) References Cited

U.S. PATENT DOCUMENTS

| | | | | |
|---|---|---|---|---|
| 4,969,176 A * | 11/1990 | Marinus | ................. | G21K 1/025 378/147 |
| 5,771,269 A * | 6/1998 | Chao | ........................ | A61B 6/06 378/147 |
| 6,031,893 A * | 2/2000 | Schmettow | ............ | G01N 23/20 378/149 |
| 6,363,136 B1 * | 3/2002 | Flisikowski | ........... | G21K 1/025 378/147 |
| 6,912,266 B2 * | 6/2005 | Spahn | ...................... | H04N 5/32 250/370.09 |
| 7,356,126 B2 * | 4/2008 | Bacher | ..................... | G21K 1/00 250/505.1 |
| 7,734,017 B2 * | 6/2010 | Zeitler | .................. | G01T 1/1644 378/154 |
| 7,751,525 B2 * | 7/2010 | Ruhrnschopf | ........ | G06T 11/005 378/7 |

(Continued)

FOREIGN PATENT DOCUMENTS

WO WO-9858389 A1 * 12/1998 ........... G03F 7/0007

*Primary Examiner* — John Villecco

(57) ABSTRACT

A device for estimating scatter in X-ray imaging is described. An anti-scatter grid with varying grid ratio is used in conjunction with an X-ray detector. The anti-scatter grid comprises attenuating lamellae that block scattered radiation. The anti-scatter grid contains regions of lesser or greater scatter rejection efficiency, which can be achieved by variations in the grid ratio. Contrast between these regions can be used to estimate residual scatter content. A method for estimating scatter from this device is further described.

6 Claims, 2 Drawing Sheets

(56) References Cited

U.S. PATENT DOCUMENTS

| | | | |
|---|---|---|---|
| 7,839,981 B2* | 11/2010 | Kammel | G21K 1/025 378/149 |
| 7,920,672 B2* | 4/2011 | Timmer | A61B 6/032 250/252.1 |
| 8,041,096 B2* | 10/2011 | Bernhardt | A61B 6/00 378/62 |
| 8,121,249 B2* | 2/2012 | Wang | A61B 6/032 378/6 |
| 8,433,154 B2* | 4/2013 | Sehnert | A61B 6/4291 382/132 |
| 8,553,831 B2* | 10/2013 | Ma | A61B 6/032 378/6 |
| 8,705,827 B2* | 4/2014 | Zhu | G06T 5/002 378/7 |
| 8,718,227 B2* | 5/2014 | Dafni | A61B 6/032 378/19 |
| 8,873,703 B2* | 10/2014 | Ruimi | A61B 6/032 250/370.09 |
| 9,001,961 B2* | 4/2015 | Star-Lack | A61B 6/032 378/7 |
| 9,134,434 B2* | 9/2015 | Niederlohner | G01T 1/17 |
| 9,196,061 B2* | 11/2015 | Hsieh | G06T 11/005 |
| 9,206,309 B2* | 12/2015 | Appleby | B22C 9/04 |
| 9,392,984 B2* | 7/2016 | Pelc | A61B 6/4035 |
| 9,414,792 B2* | 8/2016 | Hsieh | A61B 6/4035 |
| 9,521,982 B2* | 12/2016 | Hsieh | A61B 6/035 |
| 9,601,223 B2* | 3/2017 | Deych | G21K 1/025 |
| 9,842,395 B2* | 12/2017 | Imai | G06T 7/0012 |
| 2009/0003530 A1* | 1/2009 | Van Vroonhoven | G01N 23/04 378/154 |
| 2009/0185655 A1* | 7/2009 | Koken | A61B 6/032 378/11 |
| 2012/0163554 A1* | 6/2012 | Tada | A61B 6/4035 378/154 |
| 2017/0265822 A1* | 9/2017 | Du | A61B 6/03 |
| 2018/0000431 A1* | 1/2018 | Roth | A61B 6/4429 |

* cited by examiner

X-RAY ANTI-SCATTER GRID WITH VARYING GRID RATIO

CROSS REFERENCE TO RELATED APPLICATIONS

This application claims priority under 35 U.S.C. § 119 from U.S. Provisional Patent Application No. 62/134,991, filed Mar. 18, 2015, entitled ANTI-SCATTER GRID WITH STRIPED GRID RATIO, which is incorporated herein by reference for all purposes.

GOVERNMENT RIGHTS

This invention was made with Government support under contract EB015574 awarded by the National Institutes of Health. The Government has certain rights in this invention.

BACKGROUND OF THE INVENTION

This invention relates generally to X-ray imaging, including diagnostic radiography and computed tomography (CT). Specifically, the invention relates to the use of X-ray anti-scatter grids to improve image quality.

In X-ray imaging, primary radiation photons are emitted from an X-ray source towards an X-ray detector. They pass through an object to be imaged. Some of the photons are scattered within the object and are re-directed towards another path. These scattered photons arrive at the detector at random directions and add an overlying haze to the image, reducing image quality or creating artifacts.

Anti-scatter grids are often employed to reduce the detection of scattered radiation. Anti-scatter grids comprise lamellae, or plates of X-ray attenuating material, that are parallel to the ray path between source and detector. The placement of these lamellae causes them to selectively block scattered radiation over primary radiation. However, residual scatter remains even with an anti-scatter grid. The residual scatter can still cause artifacts.

It would therefore be valuable to have a mechanism for estimating the scatter that remains even after the anti-scatter grid.

SUMMARY OF THE INVENTION

An anti-scatter grid with varying grid ratio is described. In one embodiment, this anti-scatter grid consists of a first set of regions with decreased scatter rejection efficiency and a second set of regions with increased scatter rejection efficiency. Changing the scatter rejection can be achieved by changing the grid ratio. Existing anti-scatter grid designs seek to keep the grid ratio uniform throughout the grid. However, by introducing sharp changes in the grid ratio, we effectively modulate the scatter content and create contrast between the first set of regions and the second set of regions, which can be exploited to estimate the residual scatter content.

A method for estimating scatter using an anti-scatter grid with varying scatter rejection efficiency is also described. Varying scatter rejection efficiency can be achieved through the use of varying grid ratios. Regions of the image with lower and higher rejection efficiency are used. The interfaces between these two regions show contrast from the differential scatter rejection efficiencies, and these can be used to infer the local scatter content. If an image of the scatter content across the entire grid is desired, a smooth interpolation method can be used.

DETAILED DESCRIPTION OF ILLUSTRATED EMBODIMENTS

X-ray anti-scatter grids are devices which comprise highly attenuating lamellae (e.g. lead plates) which are focused towards the source. In between the lamellae there may be interstitial material designed to provide mechanical support, but which is minimally attenuating. X-ray photons which arrive from the source are preferentially passed through the anti-scatter grid, unless they intersect the lamellae themselves. X-ray photons which are scattered in the object being scanned typically arrive from a random direction and are preferentially absorbed by the grid. These anti-scatter grids are widely used to reduce scatter and thereby improve image quality. The grid ratio of the grid is defined to be the height of the lamellae divided by the distance between two adjacent plates. Increasing the grid ratio of the grid increases the scatter rejection efficiency of the anti-scatter grid.

In existing designs, the grid ratio is essentially constant throughout the usable area of the grid. However, an anti-scatter grid with a varying grid ratio, comprising sections with higher grid ratio (and therefore higher scatter rejection, and less detected scatter) and sections with lower grid ratio can be used for the purpose of creating contrast in the detected image directly related to the residual scatter. This anti-scatter grid with varying grid ratio can be used not only to suppress some incident scatter by direct absorption, but also to give the system the capability of estimating the residual scatter.

Figure 1:
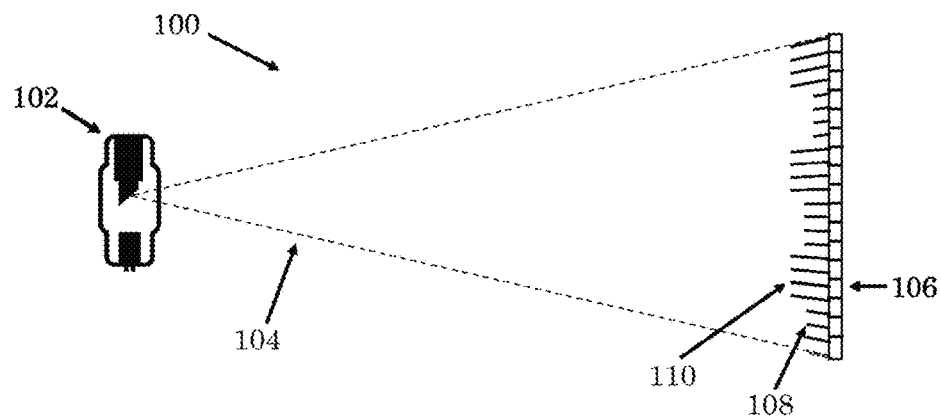
FIG. 1 shows an X-ray imaging arrangement with shows a schematic of the anti-scatter grid with varying grid ratio.

FIG. 1 is a schematic of an X-ray imaging system using an anti-scatter grid with varying grid ratio. The imaging system 100 comprises an X-ray source 102, an X-ray detector 106, and the anti-scatter grid which comprise lamellae. The X-ray source casts a fan of radiation 104 directed towards the detector. Existing designs for anti-scatter grids use substantially the same grid ratio for all the lamellae. The anti-scatter grid with varying grid ratio includes regions with lamellae of reduced grid ratio 108, and regions of lamellae with increased grid ratio 110. Changes in grid ratio could be achieved, for example, by modifying the height of the lamellae, or by changing the spacing between lamellae. In some designs, the lamellae of the grid lie on top of space between detector pixels. In other designs, this is not possible. In the latter case, it may be desirable to vary the grid ratio by changing the spacing between lamellae instead of changing the height, in order to decrease the number of primary photons absorbed by the lamellae and hence improve the dose efficiency of the scanner.

In one preferred embodiment, regions of reduced grid ratio will alternate with regions of increased grid ratio, effectively producing stripes of lesser and greater scatter rejection. To further simplify the design, these regions will span the entire length or the entire width of the grid. Therefore, along one dimension the grid ratio is constant, and along the other dimension the grid ratio is striped in alternating higher and lower grid ratio. For brevity, we will refer to this preferred embodiment simply as a "striped ratio grid." The stripe pattern can be immediately discerned in the presence of scatter and can be used to estimate and subsequently remove scatter.

Grids with varying grid ratio present a simple and direct option for measuring scatter in projection images. Unlike other software scatter estimation algorithms, these grids make few assumptions on the object and can be used in conjunction with unpredictable scanning arrangements, such as dynamic bowtie filters, or when imaging irregular objects, as in industrial CT. Besides the stripe pattern described above, other grid designs could be employed which provides transitions in the detected scatter-to-primary ratio. As a more complicated example, a sinusoidal variation could be used, and frequency based techniques would be used to extract the scatter content from the resulting images.

One challenge with striped ratio grids is differentiating between scatter and primary variation across the transition. One might expect that a sophisticated image processing algorithm would be necessary to manage the problem of primary variation. We will describe a fairly simple algorithm to illustrate that extracting scatter content does not require fine tuning or complicated processing. More sophisticated algorithms could be developed to improve performance and robustness.

Let $x_1$ be the signal in a pixel in a low scatter region (one with high grid ratio, and hence high scatter rejection efficiency), and $x_2$ be the signal in a pixel high scatter region (one with low grid ratio). We assume the detector image has been dark and gain corrected. The pixels corresponding to $x_1$ and $x_2$ are nearby, but not necessarily adjacent. An estimate of the scatter content near $x_1$ and $x_2$ is determined by $k(x_2-x_1)$, where k is a proportionality constant related to the relative scatter rejection efficiencies in the two regions. For example, if the scatter rejection efficiency in the low scatter region was 70%, and the scatter rejection efficiency in the high scatter region was 50%, and the primary acceptance in both regions was identical, the scatter contrast between the two regions would be 20% of the original scatter and we would choose k=5. The scatter rejection efficiency may also vary with the object being scanned and the scan protocol, including the tube voltage.

To correct for primary variation, one may obtain a second estimate of the scatter content using two other signals $x_0$ and $x_3$, which correspond to other pixels in the low and high scatter regions, respectively. In one embodiment, x1 and x2 correspond to adjacent pixels that straddle the border between the low and high scatter regions, whereas x0 and x3 correspond to pixels that are several pixels distant from the border. A second estimate of the scatter may be determined using $k(x_3-x_0)$. When the two estimates of scatter are inconsistent, the scatter estimate is rejected.

In some cases, the signals for $x_0$, $x_1$, $x_2$, and $x_3$ may undergo preprocessing, such as averaging or smoothing to reduce the effect of stochastic noise. Smoothly varying change in primary radiation could also be estimated and used as a correction.

The consistent estimates of scatter that remain can be used to estimate the scatter in the entire image using a smooth interpolation method such as gridding. The scatter can then by scaled by 1 minus the scatter rejection efficiency for each pixel to estimate the scatter that remains after the anti-scatter grid. This can be used to correct the projection image.

To validate the effectiveness of these anti-scatter grids, we performed experiments on a tabletop CT system. Data for an anti-scatter grid with varying grid ratio was emulated using two subsequent scans of the same object with different scatter rejection efficiencies from different grid configurations, with the detector data spliced together to mimic the effect of the striped ratio grid.

Figures 2A, 2B:
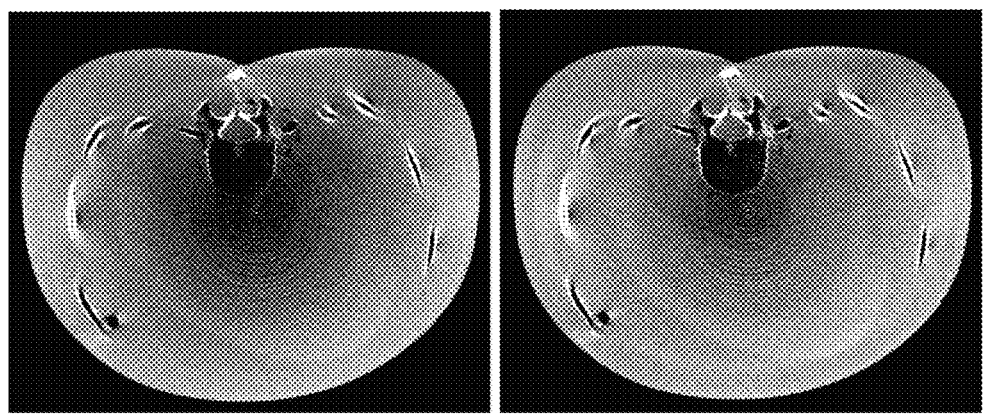
FIG. 2A shows a CT image reconstructed with a conventional anti-scatter grid.
FIG. 2B shows a CT image reconstructed with an anti-scatter grid with varying grid ratio, having estimated and eliminated the residual scatter content.

FIG. 2A shows a CT reconstruction with a conventional anti-scatter grid without varying grid ratio. FIG. 2B shows a CT reconstruction using the proposed anti-scatter grid with varying grid ratio, including the correction for residual scatter. A reduction in cupping artifacts is observed, demonstrating the improvement possible with this concept.

Figure 3A:
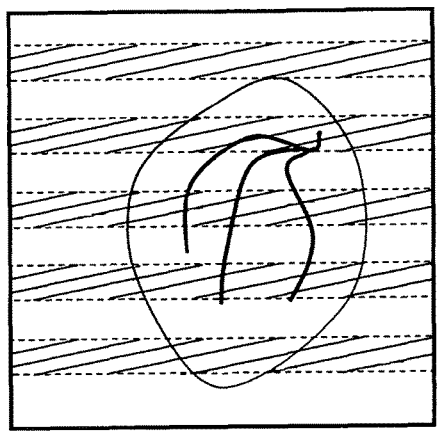
FIG. 3A shows a projection X-ray image taken with an anti-scatter grid with varying grid ratio.
Figure 3B:
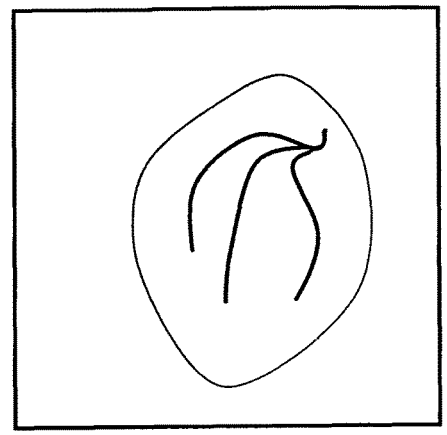
FIG. 3B shows the corrected image, having estimated and eliminated the residual scatter content.

FIG. 3A shows an individual projection image of the striped grid ratio prior to correction. The stripes in the image are created by differential scatter rejection efficiencies along the stripes. FIG. 3B show the corrected images, after the scatter content has been estimated and subtracted out from the image. The resulting image has improved contrast than could be achieved with a standard anti-scatter grid.

What is claimed is:

1. An anti-scatter grid with varying grid ratio for x-ray imaging comprising:
   a plurality of regions, wherein each region comprises two or more lamellae with the same grid ratio;
   wherein the grid ratio characterizing any region of the plurality of regions is distinct from the grid ratio of any neighboring region;
   wherein at least three regions of the plurality of regions possess a grid ratio that is greater than any neighboring region.

2. A method of estimating scatter from an X-ray image, comprising:
   recording an image using an X-ray detector and anti-scatter grid, wherein the anti-scatter grid has non-uniform scatter rejection efficiency;
   identifying a plurality of location pairs within the image, wherein each location pair consists of a first location and a second location, with the second location having a greater scatter rejection efficiency than the first;
   estimating scatter using differences in detected signal at the first and second location of each location pair.

3. The method, as recited in claim 2, wherein the first and second location in each location pair are chosen to be in close spatial proximity.

4. The method, as recited in claim 3, further comprising the step of discarding scatter estimates which are deemed inconsistent.

5. The method, as recited in claim 4, further comprising the step of estimating scatter content throughout the image using a smooth interpolation method.

6. The method, as recited in claim 5, wherein the smooth interpolation method is gridding.

* * * * *